United States Patent
Noble

(10) Patent No.: US 9,636,202 B2
(45) Date of Patent: May 2, 2017

(54) SUPPORT FOR EAR BASE

(71) Applicant: Poriferous, LLC, Newnan, GA (US)

(72) Inventor: Aaron Noble, Newnan, GA (US)

(73) Assignee: Poriferous, LLC, Newnan, GA (US)

( * ) Notice: Subject to any disclaimer, the term of this patent is extended or adjusted under 35 U.S.C. 154(b) by 0 days.

(21) Appl. No.: 14/802,382

(22) Filed: Jul. 17, 2015

(65) Prior Publication Data

US 2016/0015502 A1    Jan. 21, 2016

Related U.S. Application Data

(60) Provisional application No. 62/025,919, filed on Jul. 17, 2014.

(51) Int. Cl.
*A61F 2/18* (2006.01)
*A61F 2/00* (2006.01)

(52) U.S. Cl.
CPC .............. *A61F 2/0059* (2013.01); *A61F 2/18* (2013.01); *A61F 2002/183* (2013.01)

(58) Field of Classification Search
CPC ............................. A61F 2/18; A61F 2002/183
USPC ...................................... 623/10, 23.71–23.72
See application file for complete search history.

(56) References Cited

U.S. PATENT DOCUMENTS

| 5,433,748 A | 7/1995 | Wellisz |
| 2014/0364946 A1* | 12/2014 | Chen ......................... A61F 2/50 623/10 |
| 2015/0238324 A1* | 8/2015 | Nebosky ................. A61F 2/447 623/17.16 |

FOREIGN PATENT DOCUMENTS

SU             683737 A1      9/1979

OTHER PUBLICATIONS

International Search Report and Written Opinion, PCT Application No. PCT/US2015/040915, mailed Oct. 8, 2015.
International Preliminary Report on Patentability, PCT International Patent Application No. PCT/US2015/040915, mailed Jan. 26, 2017, 7 pages.

* cited by examiner

*Primary Examiner* — Katrina Stransky
*Assistant Examiner* — Wade P Schutte
(74) *Attorney, Agent, or Firm* — Kilpatrick Townsend & Stockton LLP

(57) ABSTRACT

Embodiments of the invention described herein thus provide systems and methods for ear restoration surgery. Certain embodiments provide an improved framework that provides enhanced cooperation between an ear base and a rim.

22 Claims, 5 Drawing Sheets

SUPPORT FOR EAR BASE

CROSS REFERENCE TO RELATED APPLICATIONS

This application claims the benefit of U.S. Provisional Application Ser. No. 62/025,919, filed Jul. 17, 2014, titled "Support for Ear Base," the entire contents of which are hereby incorporated by reference.

FIELD OF THE DISCLOSURE

Embodiments of the present disclosure relate generally to a support for an ear base that is used in ear restoration and reconstruction.

BACKGROUND

Surgical reconstruction of an external ear often uses a framework implant. The framework implant can be used to support the patient's overlying skin and generally provides a cartilage-like support structure, providing predictable aesthetic results. Porous polyethylene ear implants have been used for many years as a framework material. This material generally has good biocompatibility for reconstruction of ear malformations. Due to its porous structure, the material can promote revascularization at the implantation site. However, there are some drawbacks with currently available frameworks, and improvements are desired.

BRIEF SUMMARY

Embodiments of the invention described herein thus provide systems and methods for ear restoration surgery. Certain embodiments provide an improved framework that provides enhanced cooperation between an ear base and a rim.

Certain examples provide an ear base for an ear implant restoration, which has an ear base body comprising an antihelix rib and a rearwardly extending flange; and a support tab extending from the ear base. The support tab may extend from a point between the anti-helix rib and the rearwardly extending flange. The support tab may extend from a location where the inferior crus and superior crus of the ear base meet. The ear base and the support tab may comprise porous polyethylene. Exemplary polyethylenes include but are not limited to high density polyethylene or ultra high molecular weight polyethylene (UHMWPE). The ear base and the support tab may comprise polyether ether ketone (PEEK), polyethylene terephthalate (PETE), nylon, polypropylene, or any polymer of aliphatic hydrocarbons containing one or more double bonds, or any combination thereof. In one example, the support tab may have a reinforcing support rib. In another example, the support tab may be a thickened tab. The support tab can have a rectangular-like shape, or any other appropriate shape. Further examples provide an ear implant restoration device, which has a flexible rim, an ear base body, and a support tab extending from the ear base body.

DETAILED DESCRIPTION

Figure 1:
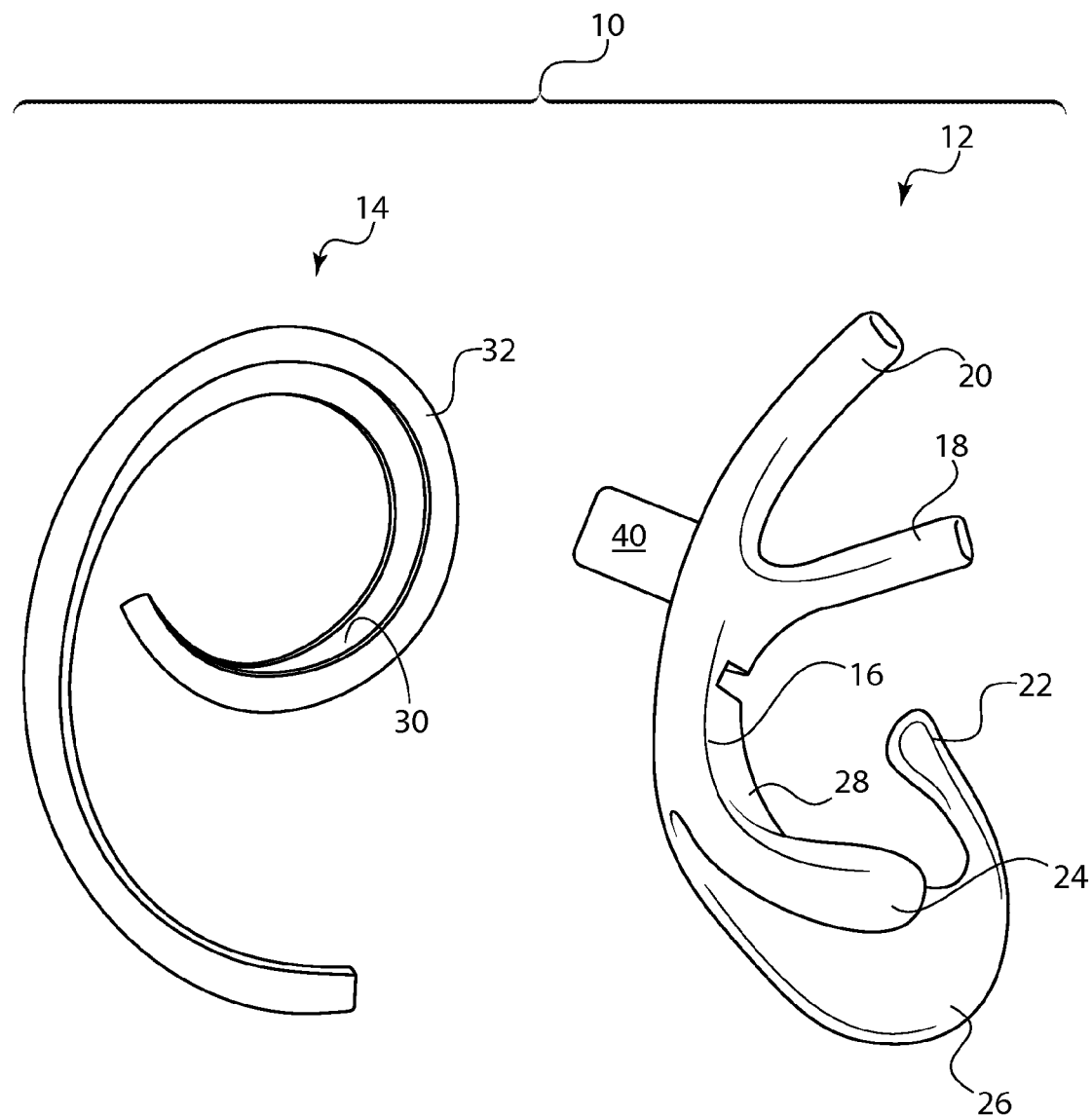
FIG. 1 shows a side perspective view of a rim and an ear base according to embodiments described herein.

An ear implant made of porous polyethylene or other porous material can provide a porous structure that allows tissue ingrowth. The material may be easily moldable, such that scalpels or heating can design and form structure interoperatively. Embodiments described herein provide improved cooperation between various components of ear implants.

Embodiments of the present invention provide a support for an ear base that is used in ear restoration. A framework ear implant 10 generally includes two main components— the ear base 12 and a rim 14. The ear base 12 is generally shaped to resemble a patient's outer ear. It includes an antihelix rib 16, an inferior crus 18, a superior crus 20, a tragus element 22, and an antiragus element 24. A lower portion of the ear base also features a lobule 26, which forms the ear lobe. An implant flange 28 extends rearwardly from the antihelix rib 16. The implant flange 28 can help assist with implant placement in use.

Figure 2:
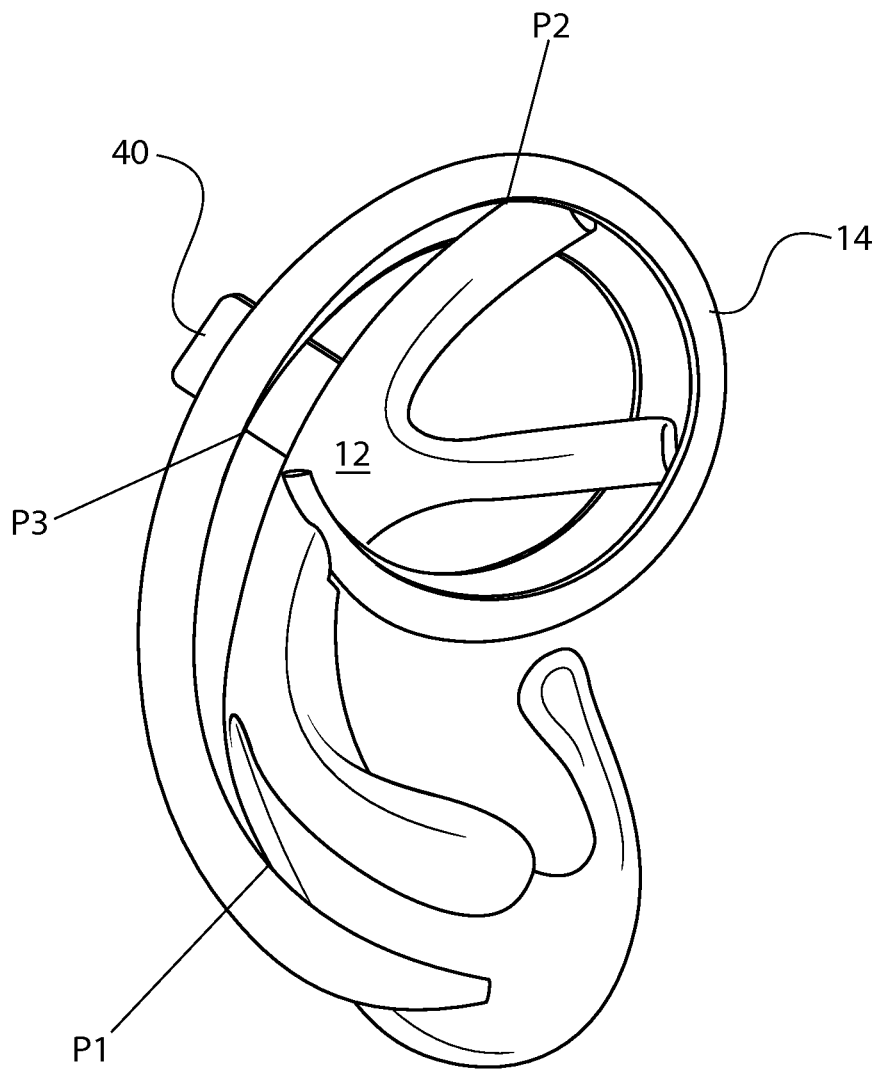
FIG. 2 shows a side perspective view of rim and an ease base in cooperation with one another.

Referring now to the rim 14, the rim 14 is designed to resemble the outer curvature of the ear, called the helix. It is generally a flexible element that can be twisted as desired. The rim 14 is formed as an elongated element with a hollow interior 30, which resembles a C-shape in cross-section. The rim 14 also has an upper curve 32, which forms the upper and outer portion of the ear helix. The rim 14 may help adjust the size of the ear that is reconstructed by sliding along the antihelix rib 16 of the ear base, and then be secured thereto at the appropriate position, once the appropriate ear size and shape has been formed. FIG. 2 illustrates an exemplary cooperation between the ear base 12 and the rim 14. As shown, there are generally two connection points between the ear base 12 and the rim 14, illustrated as P1 and P2. Once positioned as desired, the components 12, 14 may be bound together by heating with a point welding or cautery device or suturing. The general goal is for the contours to match as closely as possible so that a mirror image of the healthy ear may be formed.

However, the present inventor has found that during implant surgery, it may be the case that the rim 14 and the ear base 12 are not easily attached in the desired position. It may also be the case that connection points P1 and P2 are insufficient for the desired securement. Accordingly, there is provided a support tab 40 extending away from the ear base 12. The support tab 40 may provide at least a third connection point, P3, between the ear base 12 and the rim 14. In use, the support tab 40 may provide at least one additional point of attachment between the ear base 12 and the rim 14. As described in more detail below, it is possible to provide more than one support tab 40.

Figure 3:
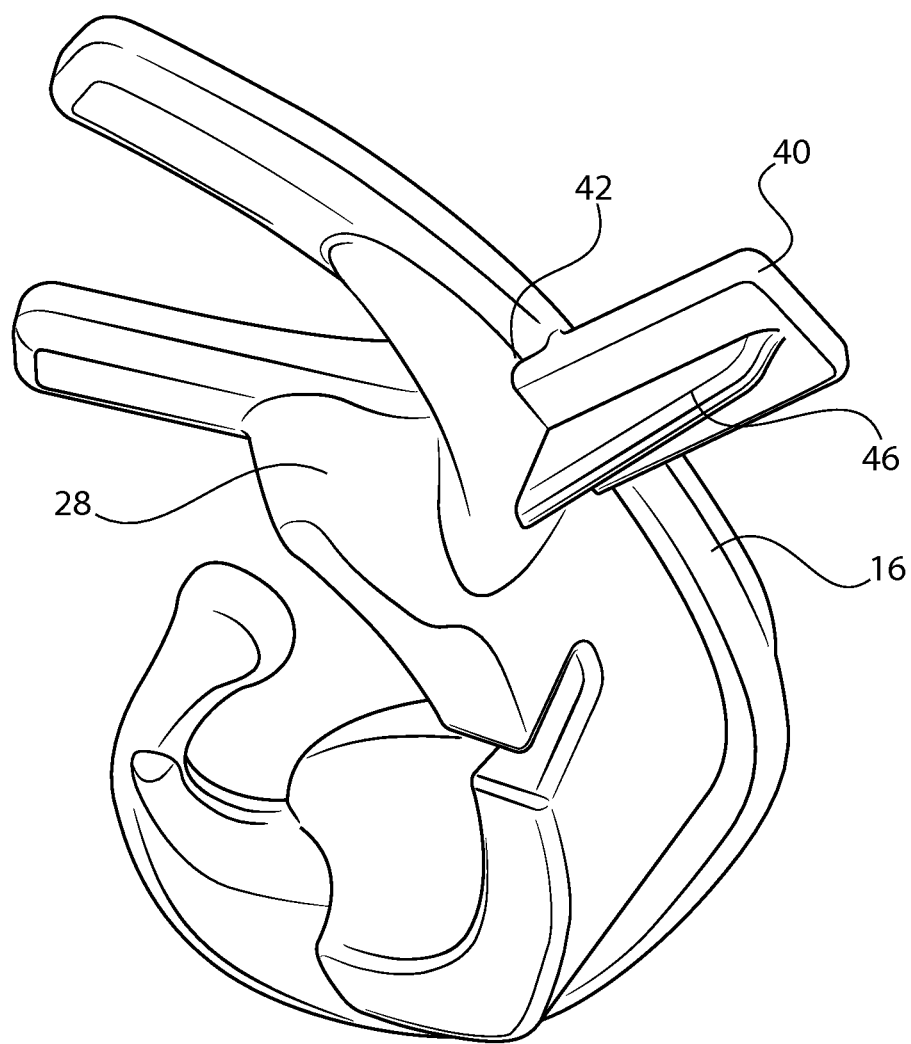
FIG. 3 shows a rear perspective view of an ear base, illustrating the rear flange and one example of a potential extension location for the support tab.
Figure 4:
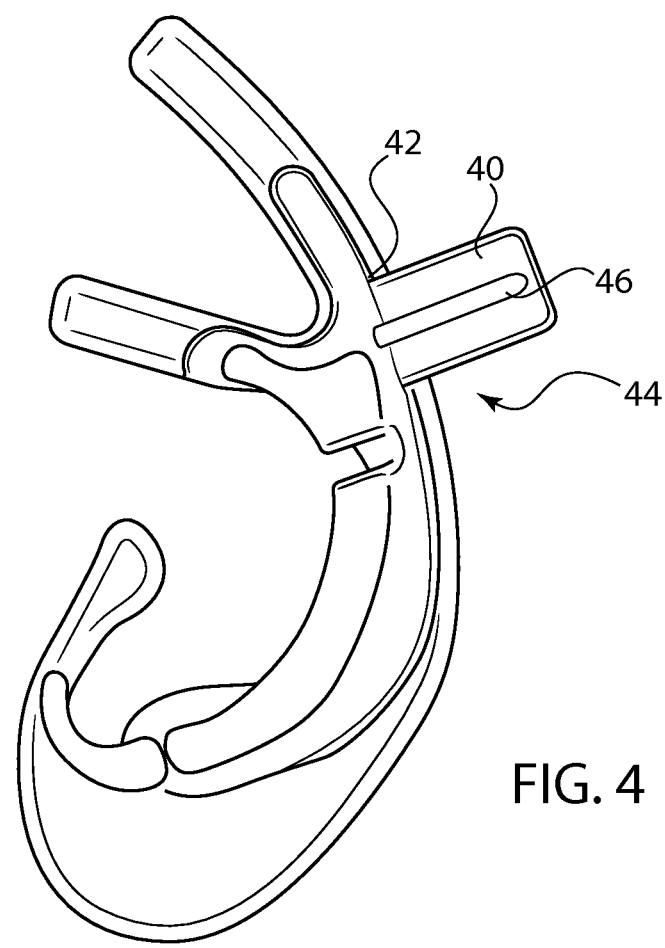
FIG. 4 shows a front perspective view of the ear base of FIG. 3.
Figure 5:
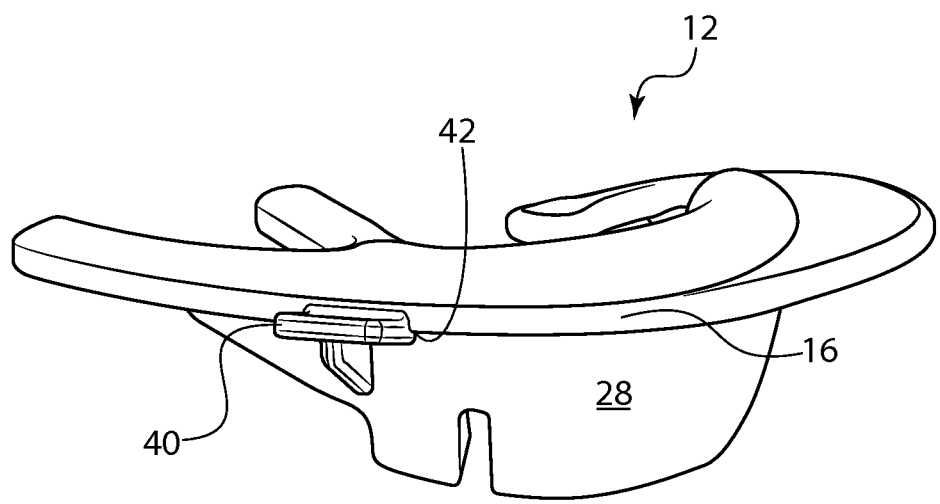
FIG. 5 shows a side perspective view of the ear base of FIG. 3.

In one example, the support tab 40 may be attached to or otherwise cooperate with the antihelix rib 16. As is shown in FIGS. 3 and 4, the support tab 40 may extend from a cooperation point 42 between the antihelix rib 16 and the flange 28. This position can prevent interruption of the shape of the antihelix rib 16 (such that it shows through the repositioned, overlying skin) while providing an appropriate cooperation point with the rim 14. In other words, the support tab 40 is positioned somewhat behind the antihelix rib 16 so as not to interfere therewith. One example of this position is illustrated by FIG. 5.

Figure 6A:
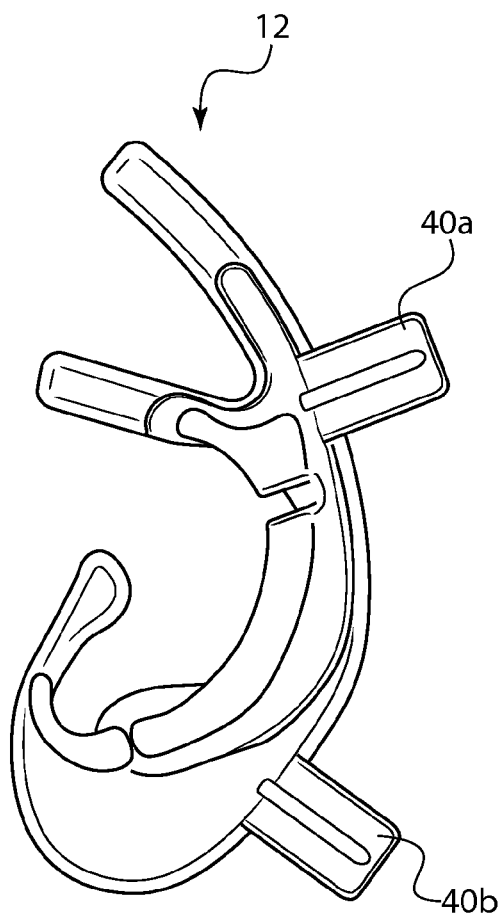
FIG. 6A shows a rear perspective view of an alternate ear base, which has two support tabs.
Figure 6B:
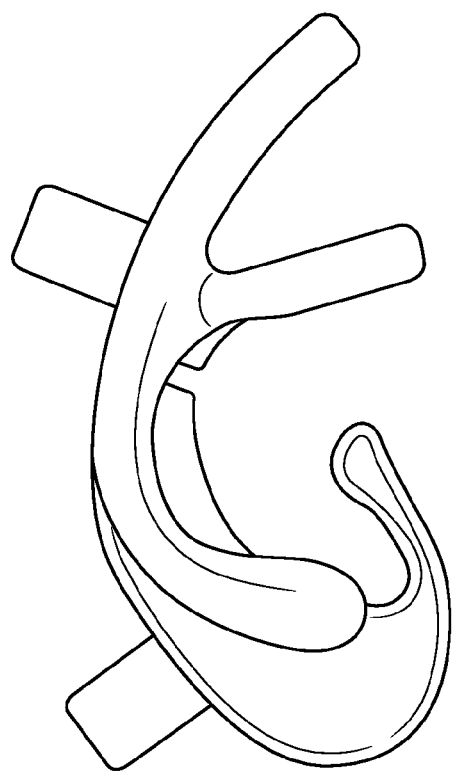
FIG. 6B shows a front perspective view of the ear base of FIG. 6A.

The support tab 40 may extend from the ear base 12 from the location 44 at which the inferior crus 18 and superior crus 20 meet. In another example, the support tab 40 may extend from the ear base 12 at a point superior to location 44. In a further example, the support tab 40 may extend from the ear base 12 at a point inferior to location 44, between the inferior crus 18 and the lobule 26. Additionally, multiple support tabs 40 may be provided in various positions along the antihelix rib 16. One example of this embodiment is shown by FIGS. 6A and 6B. FIG. 6A illustrates a rear perspective view of an ear base 12 having a first support tab 40a and a second support tab 40b. FIG. 6A shows a front perspective view. Although two support tabs 40a and 40b are shown in these figures, it should be understood that more support tabs may be provided. It may be desirable to provide three support tabs, four support tabs, five support tabs, or more. It may also be possible to provide an elongated support tab that runs the edge of the ear base.

In one example, the support tab 40 may be provided with a support rib 46. The support rib 46 is shown as generally extending along a central portion of a rearward surface 48 of the support tab 40. The support rib 46 may be provided as a raised protrusion, which may provide additional support to the support tab 40 in use. In another example, the support tab 40 may have its entire body provided as a thickened tab. The support tab may have a rectangular-like shape, a square-like shape, an oval-like shape (such that its non-connected end is curved), a pyramidal shape, a circular shape, or any other appropriate shape. The support tab 40 may have curved edges. The general goal is for the support tab to provide a support face 50 along which the rim 14 can rest.

In one example, the support tab may be about 0.85 mm thick. In other examples, it may have a thickness of about 0.5 mm, about 1.0 mm, about 1.5 mm, about 2.0 mm, about 2.5 mm, about 3.0 mm, about 4.0 mm, about 5.0 mm, about 5.5 mm, about 6.0 mm, about 6.5 mm, about 7.0 mm, or about 8 mm. This list is provided for exemplary purposes only and it should be understood that other thicknesses within these ranges as well as outside these ranges are possible and considered within the scope of this disclosure. Potential ranges for the projection length of the support tab include but are not limited to from about 3.0 mm to about 15.0 mm. For example, the support tab may project from the ear base about 3.0 mm, about 4.0 mm, about 5.0 mm, about 6.0 mm, about 7.0 mm, about 8.0 mm, about 9.0 mm, about 10.0 mm, about 11.0 mm, about 12.0 mm, about 13.0 mm, about 14.0 mm, or about 15 mm. This list is provided for exemplary purposes only and it should be understood that other projection lengths within these ranges as well as outside these ranges are possible and considered within the scope of this disclosure. In one specific example, the support tab 40 may be about 5 mm wide and about 5 mm in length/projection.

In use, the rim 14 overlays the support tab 40 and rests along the support face 50. Once the surgeon has located the rim 14 with respect to the ear base 12 at the desired position, s/he may heat weld or suture or otherwise secure the rim 14 to the support tab 40. In one specific embodiment, it is possible for the surgeon to trim any excess material of the support tab 40 that may extend beyond the rim 14. This trimming step is not required, however, particularly if the tab is provided as a thickened tab that is not easily trimmed or otherwise cut or shaped.

The support tab 40 may be formed integrally with the ear base 12, such that the particles forming the implant 10 are all sintered in the same mold. It is also possible for the support tab 40 to be welded or otherwise attached to the ear base 12 subsequent to formation of the ear base 12.

Although the support tab 40 has been described for use in connection with a porous polyethylene implant, it should be understood that the ear base 12 may be any known or future developed ear base. It is generally expected that the support tab 40 will be formed as having the same material as the ear base. However, it should be understood that it is possible for the support tab to be formed from a different material instead. In one example, the ear base 12 and the support tab 40 may be constructed from a high density polyethylene that either has an inter-connected pore structure or a smooth nonporous structure. One potential polyethylene is high density polyethylene or ultra high molecular weight polyethylene (UHMWPE). Other potential materials include but are not limited to polyether ether ketone (PEEK), polyethylene terephthalate (PETE), nylon, polypropylene, or any polymer of aliphatic hydrocarbons containing one or more double bonds, and allow the implant to be at least partially pliable. Other materials are also possible and considered within the scope of this disclosure. Combinations of these and other materials are also possible.

Changes and modifications, additions and deletions may be made to the structures and methods recited above and shown in the drawings without departing from the scope or spirit of the disclosure or the following claims.

What is claimed is:

1. An ear base for an ear implant restoration, comprising:
    an ear base body comprising a superior crus, an inferior crus, and an antihelix rib; and
    at least one support tab extending from and integrally formed with the ear base along the antihelix rib.

2. The ear base of claim 1, wherein the ear base further comprises a rearwardly extending flange, and wherein the at least one support tab extends outwardly from the ear base from a point between the anti-helix rib and the rearwardly extending flange.

3. The ear base of claim 1, wherein the ear base comprises a lobule, wherein the at least one support tab is located along the ear base between the superior crus and the lobule.

4. The ear base of claim 1, comprising a plurality of support tabs.

5. The ear base of claim 1, wherein the support tab extends from a location where the inferior crus and superior crus meet.

6. The ear base of claim 1, wherein the ear base and the support tab comprise porous polyethylene, polyether ether ketone, polyethylene terephthalate, nylon, polypropylene, or a polymer of aliphatic hydrocarbons containing one or more double bonds, or combinations thereof.

7. The ear base of claim 6, wherein the polyethylene comprises high density polyethylene or ultra high molecular weight polyethylene (UHMWPE).

8. The ear base of claim 1, wherein the support tab comprises a reinforcing support rib.

9. The ear base of claim 1, wherein the support tab comprises a thickened tab.

10. The ear base of claim 1, wherein the support tab comprises a rectangular-like shape, a square-like shape, an oval-like shape, a pyramidal shape, a circular shape, or combinations thereof.

11. The ear base support of claim 1, wherein the ear base body comprises a rearwardly extending flange.

12. An ear implant restoration device, comprising:
a flexible rim,
an ear base body comprising a superior crus, an inferior crus, and an antihelix rib, and
at least one support tab extending from and integrally formed with the ear base body.

13. The ear implant restoration device of claim 12, wherein the ear base further comprises a rearwardly extending flange, and wherein the at least one support tab extends outwardly from the ear base from a point between the anti-helix rib and the rearwardly extending flange.

14. The ear implant restoration device of claim 12, wherein the ear base comprises a lobule, wherein the at least one support tab is located along the ear base between the superior crus and the lobule.

15. The ear implant restoration device of claim 12, comprising a plurality of support tabs.

16. The ear implant restoration device of claim 12, wherein the support tab extends from a location where the inferior crus and superior crus meet.

17. The ear implant restoration device of claim 12, wherein the ear base and the support tab comprise porous polyethylene, polyether ether ketone, polyethylene terephthalate, nylon, polypropylene, or a polymer of aliphatic hydrocarbons containing one or more double bonds, or combinations thereof.

18. The ear implant restoration device of claim 17, wherein the polyethylene comprises high density polyethylene or ultra high molecular weight polyethylene (UHMWPE).

19. The ear implant restoration device of claim 12, wherein the support tab comprises a reinforcing support rib.

20. The ear implant restoration device of claim 12, wherein the support tab comprises a thickened tab.

21. The ear implant restoration device of claim 12, wherein the support tab comprises a rectangular-like shape, a square-like shape, an oval-like shape, a pyramidal shape, a circular shape, or combinations thereof.

22. The ear base of claim 12, wherein the at least one support tab supports the flexible rim.

* * * * *